United States Patent [19]

Haak

[11] Patent Number: 5,503,632
[45] Date of Patent: Apr. 2, 1996

[54] ELECTROTRANSPORT DEVICE HAVING IMPROVED CATHODIC ELECTRODE ASSEMBLY

[75] Inventor: Ronald P. Haak, Menlo Park, Calif.

[73] Assignee: Alza Corporation, Palo Alto, Calif.

[21] Appl. No.: 225,125

[22] Filed: Apr. 8, 1994

[51] Int. Cl.⁶ .................................................. A61N 1/30
[52] U.S. Cl. ............................................................ 604/20
[58] Field of Search ........................... 604/20–21, 890.1; 607/149–153

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,640,689 | 2/1987 | Sibalis | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 5,057,072 | 10/1991 | Phipps | 604/20 |
| 5,084,008 | 1/1992 | Phipps | 604/20 |

FOREIGN PATENT DOCUMENTS 410009 10/1933 United Kingdom.

OTHER PUBLICATIONS

Ballestrasse, Cindy L. and Beck, Theodore R., "Acrylic Ion–Transfer Polymers", J. Electrochem. Soc.: Electrochemical Science and Technology, Nov., 1987, pp. 2745–2749, vol. 134, No. 11.

Primary Examiner—C. Fred Rosenbaum
Assistant Examiner—Mark Bockelman
Attorney, Agent, or Firm—D. Byron Miller; Steve F. Stone; Edward L. Mandell

[57] ABSTRACT

An improved cathodic iontophoresis electrode assembly (8, 38) is provided having a reducible cathodic electrode (12, 22) and a drug reservoir (14, 24) containing an anionic drug. The cathodic electrode (12, 22) is separated from the drug reservoir (14, 24) by means of a layer (30) of a cation exchange material. The cation exchange material is loaded with cations which are able to react with anions produced during reduction of the electrode (12, 22) to form an electrically neutral or substantially insoluble (eg, water insoluble) compound. The cathodic electrode (12, 22) is preferably composed of silver chloride which produces chloride ions during reduction. The cation exchange material is preferably loaded with silver or copper cations which react with the chloride ions to produce a neutral and relatively insoluble metal chloride salt.

20 Claims, 1 Drawing Sheet

ELECTROTRANSPORT DEVICE HAVING IMPROVED CATHODIC ELECTRODE ASSEMBLY

TECHNICAL FIELD

This invention relates to an improved method and apparatus for transdermal electrotransport agent delivery and more specifically, to an improved cathodic electrode assembly and to an improved method of using same to deliver an agent by electrotransport.

BACKGROUND ART

The present invention concerns devices and methods for transdermal delivery or transport of therapeutic agents by electrotransport. Herein the term "electrotransport" is used to refer to methods and apparatus for transdermal delivery of therapeutic agents, whether charged or uncharged, by means of an applied electromotive force to an agent-containing reservoir. The particular therapeutic agent to be delivered may be completely charged (ie, 100% ionized), completely uncharged, or partly charged and partly uncharged. The therapeutic agent or species may be delivered by electromigration, s electroosmosis or a combination of the two. In general, electroosmosis of a therapeutic species into a tissue results from the migration of solvent, in which the species is contained, as a result of the application of electromotive force to the therapeutic species reservoir. Still another type of electrotransport process, electroporation, involves the formation of transiently-existing pores in a biological membrane by the application of an electric field, through which pores an agent can be delivered either passively (ie, without electrical assistance) or actively (ie, under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent actually is transported.

Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the electrotransport field, indicating a renewed interest in this mode of drug delivery. For example, Vernon et al U.S. Pat. No. 3,991,755; Jacobsen et al U.S. Pat. No. 4,141,359; Wilson U.S. Pat. No. 4,398,545; and Jacobsen U.S. Pat. No. 4,250,878 disclose examples of electrotransport devices and some applications thereof. The electrotransport process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of electrotransport is in diagnosing cystic fibrosis by delivering pilocarpine salts iontophoretically. The pilocarpine stimulates sweat production; the sweat is collected and analyzed for its chloride content to detect the presence of the disease.

In presently known electrotransport devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by electrotransport. The other electrode, called the counter, indifferent, inactive or return electrode, serves to close the electrical circuit through the body. In conjunction with the patient's skin contacted by the electrodes, the circuit is completed by connection of the electrodes to a source of electrical energy, eg, a battery. For example, if the ionic substance to be delivered into the body is positively charged (ie, a cation), then the anode will be the active electrode and the cathode will serve to complete the circuit. If the ionic substance to be delivered is negatively charged (ie, an anion), then the cathode will be the active electrode and the anode will be the counter electrode.

Alternatively, both the anode and cathode may be used to deliver drugs of opposite charge, or drugs of neutral charge, into the body. In such a case, both electrodes are considered to be active or donor electrodes. For example, the anode can deliver a cationic or neutrally charged substance into the body while the cathode can deliver an anionic or neutrally charged substance into the body.

Furthermore, existing electrotransport devices generally require a reservoir or source of the beneficial agent (which is preferably an ionized or ionizable agent or a precursor of such agent) to be delivered into the body. Examples of such reservoirs or sources of agents include a pouch as described in the previously mentioned Jacobsen U.S. Pat. No. 4,250,878, or a pre-formed gel body as described in Webster U.S. Pat. No. 4,383,529 and Ariura et al U.S. Pat. No. 4,474,570. Such drug reservoirs are electrically connected to the anode or the cathode of an electrotransport device to provide a fixed or renewable source of one or more desired agents.

More recently, electrotransport delivery devices have been developed in which the donor and counter electrode assemblies have a "multi-laminate" construction. In these devices, the donor and counter electrode assemblies are formed of multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. Sibalis U.S. Pat. No. 4,640,689 discloses in FIG. 6 an electrotransport delivery device having a donor electrode assembly comprised of a donor electrode (204), a first drug reservoir (202), a semipermeable membrane layer (200), a second drug reservoir (206), and a microporous skin-contacting membrane (22'). The electrode layer can be formed of a carbonized plastic, metal foil or other conductive films such as a metallized mylar film. In addition, Ariura et al, U.S. Pat. No. 4,474,570 discloses a device wherein the electrode assemblies include a conductive resin film electrode layer, a hydrophilic gel reservoir layer, a current distribution and conducting layer and an insulating backing layer. Ariura et al disclose several different types of electrode layers including an aluminum foil electrode, a carbon fiber non-woven fabric electrode and a carbon-containing rubber film electrode.

Transdermal electrotransport delivery devices having electrodes composed of electrochemically inert materials, as well as devices having electrodes composed of electrochemically reactive materials, are known. Examples of electrochemically inert electrode materials include platinum, carbon, gold and stainless steel. Unfortunately, the use of electrochemically inert electrode materials can cause protons and oxygen gas, or alternatively hydroxyl ions and hydrogen gas, to be produced at the electrode surface through hydrolysis of water. The prior art has also recognized that the use of sacrificial (ie, electrochemically reactive) electrodes can avoid the pH changes and gas generation effects associated with the hydrolysis of water which generally accompanies the use of electrodes made from electrochemically inert materials. Electrotransport delivery devices with sacrificial electrodes are disclosed in Phipps et al U.S. Pat. Nos. 4,744,787 and 4,747,819 and Petelenz et al U.S. Pat. No. 4,752,285, incorporated herein by reference in their entirety. These patents disclose electrotransport electrodes composed of materials which are either oxidized or reduced during operation of the device. Particularly preferred electrochemically reactive electrode materials include silver as the anodic electrode, and silver chloride as the cathodic electrode. One potential disadvantage of these electrochemically reactive electrodes, is that once they are oxidized or reduced, they produce extraneous ions of the same charge as the drug ions. The extraneous ions can compete with the drug ions for carrying current from the device into the body, thereby lowering the drug delivery efficiency of the device. For example, when using a silver anode to deliver a cationic drug, the operation of the device causes the silver electrode to be oxidized according to the following reaction:

$$Ag \rightarrow Ag^+ + e^-$$

If left to freely migrate, the silver ions produced in the oxidation reaction will compete with the drug cations for delivery into the body. U.S. Pat. Nos. 4,744,787; 4,747,819; and 4,752,285 deal with the problem of extraneous silver ions by compounding the drug as a chloride or hydrochloride salt. The silver ions react with the drug counter ions (ie, chloride ions) to produce silver chloride which is substantially insoluble in water, thereby removing the extraneous silver ions from solution. Since many drugs are manufactured and sold in hydrochloride salt forms, this represents a practical solution to the problem of extraneous silver ions produced during oxidation of a silver anode.

Unfortunately, the extraneous ions generated by reduction of silver chloride cathode are not so practically controlled. When a silver chloride cathodic electrode is used to deliver a drug (eg, an anionic drug), the operation of the device causes the silver chloride electrode to be reduced according to the following reaction:

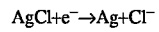

$$AgCl + e^- \rightarrow Ag + Cl^-$$

If left to freely migrate, the extraneous chloride ions produced during reduction of the silver chloride electrode will compete with the drug (eg, drug anions) for delivery into the body. Most anionic drug salts are formulated as alkali metal salts or alkaline earth metal salts, most typically as sodium salts. Since most alkali metal chloride and alkaline earth metal chloride salts have good water solubility, the extraneous chloride ions produced by the cathodic reduction do not combine with the drug counter ions to form an insoluble compound. While silver chloride is a substantially water insoluble chloride salt, in practice, anionic drugs which are commercially available are not formulated in the form of a silver salt.

One disadvantage of using the drug counter ion (eg, compounding a cationic drug as a hydrochloride salt or compounding an anionic drug as a silver salt) in order to control extraneous ions produced by oxidation or reduction reactions (eg, oxidation of a silver anode or reduction of a silver chloride cathode), is the fixed supply of drug counter ion which can be placed in the system. Under certain conditions of operation, the amount of free chloride counter ions (or free silver counter ions) may be insufficient to bind all of the extraneous ions being produced by oxidation/reduction at the electrode. Thus, under certain conditions of operation, the electrode/drug salt formulation disclosed in the Phipps et al and Petelenz patents may not be able to effectively remove all of the extraneous ions, eventually resulting in a lowered drug delivery efficiency from the device.

An alternative approach to avoiding the adverse effects associated with extraneous ions produced at the donor electrode of an electrotransport delivery device is disclosed in Sanderson et al, U.S. Pat. No. 4,722,726. This patent discloses an electrode assembly having an upper chamber filled with a salt solution and a lower chamber containing the drug solution. The upper chamber is separated from the lower chamber by means of an ion exchange membrane. The ion exchange membrane is impermeable to the passage of drug ions and ions having the same charge as the drug ions and thereby prevents the drug from entering the upper chamber. Likewise, the membrane prevents ions produced at the electrode surface which have the same charge as the drug ions (ie, either protons or hydroxyl ions in the case of an electrochemically inert electrodes, or metal ions such as silver ions or halide ions such as chloride ions in the case of an electrochemically reactive electrode material) from entering the lower chamber and competing with the drug ions for delivery into the body.

Accordingly, it is an objective of the present invention to provide an electrotransport agent delivery device having a cathodic electrode assembly adapted to deliver an agent such as a drug.

It is a further objective of the present invention to provide a reducible cathodic electrode assembly which effectively controls the production of extraneous anions and which therefore exhibits good drug delivery efficiency.

DISCLOSURE OF THE INVENTION

These and other objects of the present invention are met by an electrotransport agent delivery device having an improved cathodic electrode assembly. The cathodic electrode assembly includes a current distributing member comprised of silver chloride. The current distributing member is adapted to be connected to a source of electrical power and is reduced during operation of the device to form chloride ions. The electrode assembly further includes a reservoir containing an agent to be delivered. The reservoir is electrically connected to the current distributing member and is adapted to be placed in agent transmitting relation with a body surface of a patient. A discrete layer consisting essentially of a cation exchange material is positioned between the electrode and the reservoir. The cation exchange material is loaded with cationic counter ions which are capable of reacting with chloride ions to produce a substantially insoluble chloride salt. The loaded cations are preferably selected from copper and silver ions, and most preferably are silver ions.

During operation of the device, the power source causes the silver chloride current distributing member to be reduced, thereby producing chloride ions in aqueous solution within the electrode assembly. The chloride ions produced by reduction of the silver chloride current distributing member migrate (ie, by electromigration) away from the current distributing member and into the cation exchange material adjacent the current distributing member. The chloride ions react with the loaded cations (eg, silver and/or copper cations) to produce an insoluble, neutrally charged silver and/or copper chloride salt which has substantially no electrotransportability. Within the reservoir, the agent migrates out of the reservoir (eg, by electromigration and/or electroosmosis) into the body surface substantially without competition from the chloride ions produced during reduction of the silver chloride current distributing member.

MODES FOR CARRYING OUT THE INVENTION

Figure 1:
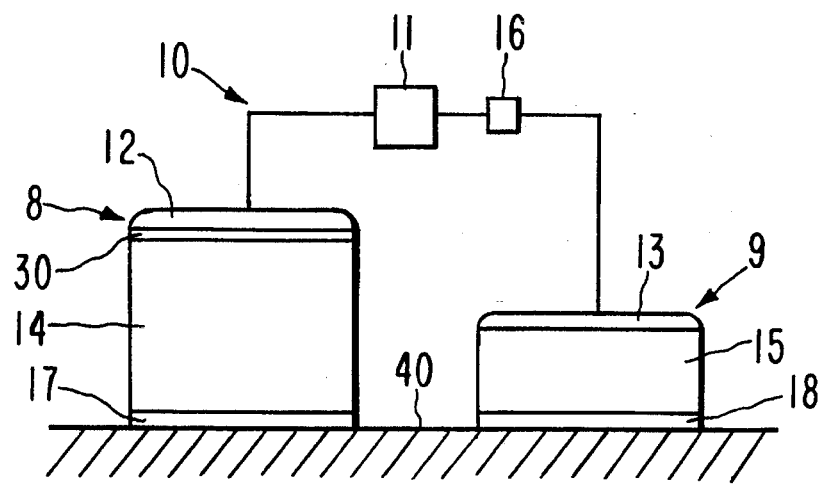
FIG. 1 is a schematic view of an electrotransport delivery device having a cathodic eletrode assembly according to the present invention.

FIG. 1 is a schematic view of an electrotransport delivery device 10 for delivering a beneficial agent through a body surface 40. Body surface 40 is typically intact skin or a mucosal membrane. Electrotransport delivery device 10 includes a donor electrode assembly 8, a counter electrode assembly 9, an electrical power source 11 (eg, a battery) and an optional control circuit 16.

The donor electrode assembly 8 includes a cathodic donor current distributing member 12 (also referred to herein as electrode 12), an agent reservoir 14 and a layer of a cation exchange material 30 positioned between electrode 12 and reservoir 14. The agent reservoir 14 contains the beneficial agent to be delivered by electrotransport from device 10. The donor electrode assembly 8 is adhered to the body surface 40 by means of an ion-conducting adhesive layer 17.

Electrotransport delivery device 10 includes a counter electrode assembly 9 which is placed on the body surface 40 at a location spaced apart from electrode assembly 8. Counter electrode assembly 9 includes an anodic current distributing member 12 (also referred to herein as counter electrode 13) and an electrolyte reservoir 15. Counter electrode assembly 9 is adhered to the body surface 40 by means of an ion-conducting adhesive layer 18. The donor and counter electrode assemblies 8 and 9 normally include a strippable release liner, not shown, which is removed prior to application of electrode assemblies 8 and 9 to body surface 40.

The electrolyte reservoir 15 contains a pharmacologically acceptable salt. Suitable electrolytes for reservoir 15 include sodium chloride, alkaline salts, chlorides, suifates, nitrates, carbonates, phosphates, and organic salts such as ascorbates, citrates, acetates and mixtures thereof. Reservoir 15 may also contain a buffering agent.

When the device 10 is in storage, no current flows because the device forms an open circuit. When the device 10 is placed on the skin or mucosal membrane of a patient and the ion-conducting portions of the device (eg, reservoirs 14 and 15, adhesive layers 17 and 18, and cation exchange layer 30) become sufficiently hydrated to allow ions to move therethrough, the circuit between the electrodes is closed and the power source begins to deliver current through the device and through the body of the patient. Electrical current flowing through the electrically conductive (ie, metallic) portions of the device 10 (ie, those portions used to connect the power source 11 to the electrodes 12 and 13)is carried by electrons (electronic conduction), while current flowing through the hydrated portions of the device 10 (eg, the cation exchange layer 30, the agent reservoir 14, the electrolyte reservoir 15 and the ion-conducting adhesive layers 17 and 18) is carried by ions (ionic conduction). In order for current to flow through the device, it is necessary for electrical charge to be transferred from electrodes 12 and 13 to chemical species by means of oxidation and reduction charge transfer reactions at the electrodes 12 and 13.

In accordance with the present invention, cathodic donor electrode 12 is comprised of silver chloride which is capable of being electrochemically reduced. Electrode 12 may take the form of a silver foil having a coating of silver chloride on the surface adjacent cation exchange layer 30. Alternatively, electrode 12 can be a polymer matrix loaded with silver chloride powder and optionally other conductive fillers such as powdered graphite, carbon fibers or the like.

Layer 30 is in intimate contact with both electrode 12 and reservoir 14 and forms an ion selective barrier therebetween. Layer 30 is comprised of a cation exchange material. Cation exchange materials are generally resins which have one or more ionizable groups bound to a polymer backbone and may contain cations which are capable of being released in exchange for other cations. Cation exchange resins may be divided into weak and strong resins, depending on the chemical functionality of the exchange group.

Usually, a cation exchange matrix, such as a cation exchange resin, consists of a rigid matrix and associated active, usually acidic, groups. One material widely used as a cation exchange matrix is a co-polymer of styrene and divinyl benzene. This copolymer is generally fabricated using suspension polymerization in an aqueous solution. The fabrication technique results in a resin in the form of small beads having tridimensional porous, rigid, and highly insoluble structures.

The degree of cross-linking within the ion exchange matrix largely determines the characteristics of the matrix. The degree of cross-linking generally varies from about 2% to about 20%, with cross-linking moderating the rigidity of the structure and the size of the pores contained within the structure. Cross-linking thus affects porosity of the resin matrix, the degree of swelling, and the rate of cationic exchange. Through control of the degree of crosslinking, the various characteristics of the cation exchange resin can be carefully chosen.

The exchange properties of resins are typically expressed by the exchange capacity in milliequivalents of exchange material per gram of dry resin. This characteristic is determined mainly by the degree of cross-linking. The exchange capacity generally runs in the range of 1 to 10 milliequivalents per gram of resin.

Another factor in the characterization of resins is the degree of swelling upon exchange of ions. The degree of swelling may vary from almost zero for so-called microreticular (ie, "gel-like") resins, to as much as twenty-five percent (25%) for macroreticular open structure materials.

As mentioned above, the ion exchange material includes an active group bound to the polymer matrix. Active groups may include groups such as sulfonic acid groups ($-SO_3H$) for strongly acidic cationic exchange resins, and carboxylic groups ($-COOH$) for weakly acidic cationic exchange resins. Typically, weakly acidic ion exchange resins are active at approximately a pH of 5 or less, whereas strongly acidic resins are active over a wide range of pH in both acidic and alkaline conditions.

Examples of cation exchange membranes are described in "Acrylic Ion-Transfer 35 Polymers", by Ballestrasse et ai, *Journal of the Electrochemical Society*, November 1987, Vol. 134, No. 11, pages 2745–2749. Additional cationic exchange membranes include sulfonated styrene polymers and sulfonated fluorocarbon polymers, such as Nation™ membranes, sold by E.I.DuPont de Nemours & Co. of Wilmington, Del.; membranes sold under the designation AR 103-QZL by Ionics, Inc. of Watertown, Mass.; cation exchange membranes sold under the designations Raipore® 4010 by RAI Research Corp. of Long Island, N.Y.; cation exchange resins sold under the designation AG 50W-X12 by Bio-Rad Laboratories of Hercules, Calif.; and cation exchange resins sold under the designation Amberlite® by Rohm and Haas, of Philadelphia, Pa. In addition to cation exchange resins, it will be readily appreciated that other types of materials capable of performing a similar function may be used. For example, nonresinous ion exchange materials in a powdered or liquid form could be used in accordance with the present invention. Such nonresinous ion exchange material would be modified by the introduction of appropriate active groups. Examples of such nonresinous ion exchange materials are cellulose, salts of heteropolyacids, and microparticulate silicas with cationic ion exchange groups. In Addition, acidic chelating resins such as Chelex resins sold by Bio-Rad Laboratories of Hercules, Calif. can also be used as the cation exchange material in layer 30.

The cation exchange material in layer 30 is compounded with a cation which can react with chloride ion to form a neutrally charged, substantially water-insoluble chloride salt. Examples of appropriate cations include metal cations such as copper (ie, cuprous but not cupric) and silver. While mercury and lead also form substantially water insoluble chloride salts, mercury and lead are preferably avoided due to their potential toxicity if inadvertently delivered to a patient. Of these metal cations, silver is most preferred due to its biocompatibility and since silver chloride has very poor water solubility. In general, the layer 30 should preferably contain a sufficient amount of cations (eg, silver ions) to effectively bind substantially all of the chloride ions produced during reduction of the silver chloride electrode 12. While the invention is not limited to any particular range of amounts of cations loaded into layer 30, it will be appreciated that even very small amounts of cations loaded into membrane 30 will have at least some beneficial effect on the drug delivery efficiency of the device. Of course, in order to maximize the drug delivery efficiency, the layer 30 most preferably contains a sufficient amount of cations to bind substantially all of the chloride ions produced during reduction of the silver chloride electrode. In order to effectively bind all of the chloride ions produced during reduction of the silver chloride electrode, the membrane 30 will most preferably contain an amount of said cations which is at least about a stoichiometric equivalent to the amount of chloride ions produced by the electrochemical reduction of the silver chloride current distributing member during the operational life (ie, the time during which a therapeutically effective amount of drug is delivered by electrotransport) of the current distributing member/electrode assembly. In use, the silver chloride electrode 12 is reduced, producing mobile chloride ions in the aqueous liquid adjacent electrode 12. The electrochemically generated chloride ions migrate away from electrode 12 (ie, by electromigration) and react with the counter ion of the cation exchange membrane 30 (eg, silver or copper cations) to form a neutrally charged, substantially insoluble silver chloride or metal chloride precipitate. The chloride salt precipitate, because of its poor water solubility and neutral charge, is not delivered, in any appreciable amounts, by electrotransport. This leaves the drug free to migrate (eg, by electromigration or electroosmosis) from reservoir 14 into the body with reduced competition from extraneous chloride anions. This results in a higher transference number for the drug, ie, more drug is delivered per unit of current applied by the device.

Figure 2:
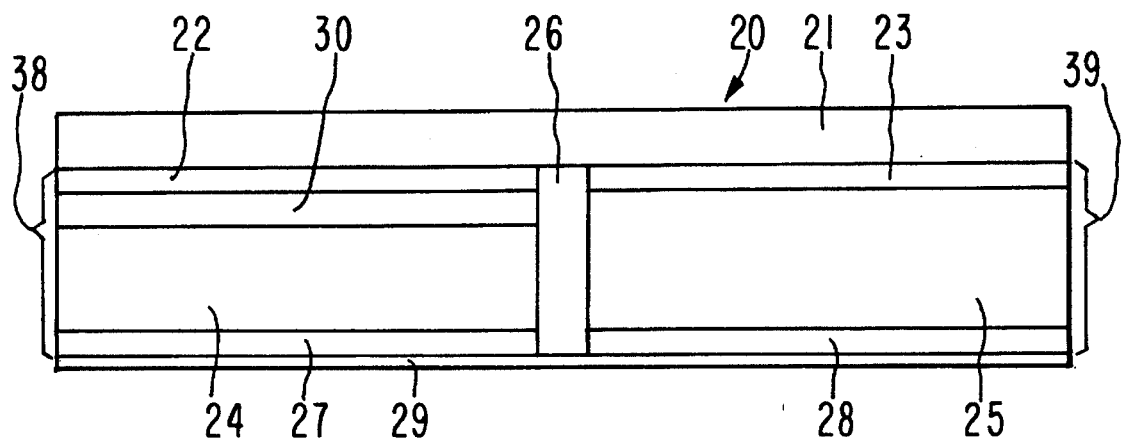
FIG. 2 is a schematic view of another electrotransport delivery device according to the present invention.

FIG. 2 illustrates one example of a preferred electrotransport delivery device 20. Device 20 has a top layer 21 which contains an electrical power supply (eg, a battery or a series of batteries) as well as optional control circuitry such as a current controller (eg, a resistor or a transistor-based current control circuit), an on/off switch, and/or a microprocessor adapted to control the current output of the power source over time.

Device 20 also includes donor electrode assembly 38 and counter electrode assembly 39. Electrode assemblies 38 and 39 are separated from one another by an electrical insulator 26, and form therewith a single selfcontained unit. The donor electrode assembly 38 includes a cathodic donor current distributing member or electrode 22, a drug reservoir 24 and a layer 30 of a cation exchange material separating the electrode 22 and the drug reservoir 24. The counter electrode assembly 39 includes an anodic counter current distributing member or electrode 23 and a return reservoir 25 which contains an electrolyte.

Electrode 23 can be formed from metal foils (eg, silver or zinc), or a polymer matrix loaded with metal powder, powdered graphite, carbon fibers, or any other suitable electrically conductive material. Reservoirs 24 and 25 can be polymeric matrices or gel matrices. Insulator 26 is composed of a nonelectrical conducting and non-ion-conducting material which acts as a barrier to prevent short-circuiting of the device 20. Insulator 26 can be an air gap, an ion impermeable polymer or adhesive or other suitable barrier to ion flow. The device 20 is adhered to the skin by means of ion-conducting adhesive layers 27 and 28. The device 20 also includes a strippable release liner 29 which is removed just prior to application to the skin.

As an alternative to the ion-conducting adhesive layers 17, 18, 27 and 28, the iontophoretic delivery devices 10 and 20 may be self-adhering to the skin in cases where the (eg, gel) matrices of reservoirs 24 and 25 are sufficiently tacky, either alone or by addition of suitable tackifying resins. Another alternative to, or to supplement the adhesiveness of, the ion-conducting adhesive layers 17, 18, 27 and 28 is an adhesive overlay. Any of the conventional adhesive overlays used to secure passive transdermal delivery devices to the skin may be used. Another alternative/supplement to the ionconducting adhesive layers 17, 18, 27 and 28, is a peripheral adhesive layer surrounding electrode assemblies 8, 9, 38 and/or 39 allowing the electrode assemblies to have a surface in direct contact with the patient's skin.

Generally, the combined skin-contacting area of electrode assemblies 8 and 9, or electrode assemblies 38 and 39, can range from about 1 cm$^2$ to greater than 200 cm$^2$, but typically will range from about 5 to 50 cm$^2$.

As an alternative to the side-by-side alignment of the donor electrode assembly 38, the insulator 26 and the counter electrode assembly 39 shown in FIG. 2, the electrode assemblies can be concentrically aligned with the counter electrode assembly 39 positioned centrally and surrounded by an annularly shaped insulator 26 which is in turn surrounded by an annularly shaped donor electrode assembly 38. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

Suitable polymers for use as the matrix of reservoirs 14, 15, 24 and 25 include, without limitation, hydrophobic polymers such as polyethylene, polypropylene, polyisoprenes and polyalkenes, rubbers such as polyisobutylene, copolymers such as Kraton®, polyvinylacetate, ethylene vinyl acetate copolymers, polyamides including nylons, polyurethanes, polyvinylchloride, cellulose acetate, cellulose acetate butyrate, ethylcellulose, cellulose acetate, and blends thereof; and hydrophilic polymers such as hydrogels, polyethylene oxides, Polyox®, Polyox® blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, and blends thereof.

The adhesive properties of the reservoirs 14, 15, 24 and 25 may be enhanced by adding a resinous tackifier. This is especially important when using a non-tacky polymeric matrix. Examples of suitable tackifiers include products sold under the trademarks Staybelite Ester #5 and #10, Regal-Rez and Piccotac, all sold by Hercules, Inc. of Wilmington, Del. Additionally, the matrix may contain a rheological agent, suitable examples of which include mineral oil and silica.

The expressions "drug" and "therapeutic agent" are used interchangeably and are intended to have their broadest interpretation as any therapeutically active substance which can be delivered by electrotransport from a cathodic donor electrode assembly to a living organism to produce a desired, usually beneficial, effect. In most cases the drug or therapeutic agent will be anionic or neutrally charged in the solution contained in the cathodic drug/therapeutic agent reservoir. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, beta-agonists, antiarrythmics, antihypertensives, ACE inhibitors, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, prostaglandins, proteins, peptides, psychostimulants, sedatives and tranquilizers.

Specific examples of anionic drugs include sodium salicylate and acetyl-salieyclic acid, non-steroidal anti-inflammatory drugs such as dieclofenac, is ketoprofen and ketorolac; heparin, certain steroids such as dexamethasone sodium phosphate, prednisolone sodium phosphate and testosterone sodium sulfate; anti-allergenics such as, sodium cromolyn; indomethacin, sodium warfarin; certain antineoplastic/antimetabolites such as methotrexate; certain antiacne compounds such as retinoic acid; certain arachidonic acid metabolites such as prostaglandins, thromboxane, prostacyclin, leukotrienes and their analogs.

The invention is also useful in the controlled delivery of peptides, polypeptides, proteins. These macromolecular substances typically have a molecular weight of at least about 300 daltons, and more typically a molecular weight in the range of about 300 to 40,000 daltons. In general, the net charge on a polypeptide or protein can be maintained negative (ie, as an anion) by maintaining the pH of the polypeptide/protein reservoir above the isoelectric point of the polypeptide/protein. Specific examples of peptides and proteins include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N=[ [(s)-4-oxo-2-azetidinyl]carbonyl]-L-histidyl-L-prolinamide ), liprecin, pituitary hormones (eg, HGH, HMG, HCG, desmopressin acetate, etc.), follicle luteolds, αANF, growth factors such as growth factor releasing factor (GFRF), βMSH, somatostatin, bradykinin, somatotropin, platelet-derived growth factor, asparaginase, bleomycin suifate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant), and TGF-beta.

Having thus generally described our invention and described in detail certain preferred embodiments thereof, it will be readily apparent that various modifications to the invention may be made by workers skilled in the art without departing from the scope of this invention which is defined only by the following claims.

I claim:

1. An electrotransport agent delivery device having a source of electrical power electrically connected to a cathodic donor electrode assembly and an anodic counter electrode assembly, the cathodic donor electrode assembly including a conductive, current distributing member comprised of reducible silver chloride, and a reservoir containing the agent to be delivered, the reservoir being electrically connected to the current distributing member and being adapted to be placed in agent transmitting relation with a body surface, wherein a discrete layer consisting essentially of a material selectively permeable to cations is positioned intermediate the current distributing member and the reservoir, the cation selective material containing cations which react with chloride ions produced during reduction of the silver chloride current distributing member to form a compound selected from a neutrally charged compound, a compound which is substantially insoluble in said reservoir, and combinations thereof.

2. The device of claim 1, wherein the cations in the cation selective material are selected from the group consisting of silver and copper cations.

3. The device of claim 1, wherein the cations in the cation selective material comprise silver ions and the neutral compound comprises silver chloride.

4. The device of claim 1, wherein the cation selective material comprises a cation exchange material.

5. The device of claim 4, wherein the cation exchange material is selected from the group consisting of polymers and copolymers having sulfonic acid or carboxylic acid groups bound to the polymer matrix.

6. The device of claim 1, wherein the cation selective material comprises a cationic chelating agent.

7. The device of claim 1, wherein the cation selective material contains an amount of said cations which is at least about a stoichiometric equivalent to the amount of chloride ions produced by the electrochemical reduction of the silver chloride current distributing member.

8. The device of claim 1, wherein the agent comprises a drug salt which is soluble to form an anionic drug ion and a cationic counter ion.

9. The device of claim 1, wherein the agent comprises a polypeptide and the reservoir contains a solution of the polypeptide at a pH above an isoelectric point of the polypeptide.

10. The device of claim 1, wherein the anodic counter electrode assembly includes a conductive current distributing member and a reservoir containing an electrolyte, the counter electrode assembly being adapted to be placed in ion transmitting relation with the body surface at a location spaced apart from the cathodic electrode assembly.

11. A method of increasing agent delivery efficiency from a cathodic electrode assembly in an electrotransport agent delivery device, the electrode assembly including a conductive current distributing member comprised of reducible silver chloride, means for connecting the current distributing member to a source of electrical power, and a reservoir containing a solution of the agent to be delivered, the reservoir being electrically connected to the current distributing member and being adapted to be placed in agent transmitting relation with a body surface, the method comprising:

loading a cation selective material with cations which are capable of reacting with chloride ions produced during reduction of the silver chloride current distributing member to form a compound selected from the group consisting of electrically neutral compounds, compounds which are substantially insoluble in said solution, and combinations thereof, and positioning a discrete layer consisting essentially of the cation selective material between the current distributing member and the reservoir.

12. The method of claim 11, wherein the cations in the cation selective material are selected from the group consisting of silver and copper cations.

13. The method of claim 11, wherein the cations in the cation selective material comprise silver ions and the neutral compound comprises silver chloride.

14. The method of claim 11, wherein the cation selective material comprises a cation exchange material.

15. The method of claim 14, wherein the cation exchange material is selected from the group consisting of polymers and copolymers having sulfonic acid or carboxylic acid groups bound to the polymer matrix.

16. The method of claim 11, wherein the cation selective material comprises a cationic chelating agent.

17. The method of claim 11, wherein the cation selective material contains an amount of said cations which is at least about a stoichiometric equivalent to the amount of chloride ions produced by the electrochemical reduction of the silver chloride current distributing member.

18. The method of claim 11, wherein the agent comprises a drug salt which is soluble to form an anionic drug ion and a cationic counter ion.

19. The method of claim 11, wherein the agent comprises a polypeptide and the reservoir contains a solution of the polypeptide at a pH above an isoelectric point of the polypeptide.

20. The method of claim 11, including delivering agent into a body surface, substantially without competition from chloride ions produced by reduction of the silver chloride current distributing member, by placing the reservoir in ion-transmitting relation with the body surface and electrically connecting the current distributing member to the power source.

* * * * *